（12） United States Patent
Ellingson et al.

(10) Patent No.: US 7,241,566 B2
(45) Date of Patent: Jul. 10, 2007

(54) METHODS AND OLIGONUCLEOTIDES FOR THE DETECTION OF *SALMONELLA* SP., *E. COLI* O157:H7, AND *LISTERIA MONOCYTOGENES*

(75) Inventors: Jay L. E. Ellingson, Marshfield, WI (US); Dirk N. Vevea, Hewitt, WI (US)

(73) Assignee: Marshfield Clinic, Marshfield, WI (US)

( * ) Notice: Subject to any disclaimer, the term of this patent is extended or adjusted under 35 U.S.C. 154(b) by 287 days.

(21) Appl. No.: 10/178,331

(22) Filed: Jun. 21, 2002

(65) Prior Publication Data
US 2003/0022214 A1 Jan. 30, 2003

Related U.S. Application Data

(60) Provisional application No. 60/373,588, filed on Apr. 18, 2002, provisional application No. 60/373,589, filed on Apr. 18, 2002, provisional application No. 60/300,199, filed on Jun. 22, 2001.

(51) Int. Cl.
C12Q 1/68 (2006.01)
C12P 19/34 (2006.01)
C07H 21/04 (2006.01)

(52) U.S. Cl. .................... 435/6; 435/91.2; 536/24.32; 536/24.3

(58) Field of Classification Search .................... 435/6, 435/91.1, 91.2
See application file for complete search history.

(56) References Cited

U.S. PATENT DOCUMENTS

| 4,689,295 | A |   | 8/1987  | Taber et al. |
| 4,992,364 | A |   | 2/1991  | Sansonetti et al. |
| 5,041,372 | A |   | 8/1991  | Lampel et al. |
| 5,043,264 | A |   | 8/1991  | Jikuya et al. |
| 5,043,272 | A |   | 8/1991  | Hartley |
| 5,130,238 | A |   | 7/1992  | Malek et al. |
| 5,298,392 | A |   | 3/1994  | Atlas et al. |
| 5,340,728 | A |   | 8/1994  | Grosz et al. |
| 5,376,528 | A |   | 12/1994 | King et al. |
| 5,389,513 | A |   | 2/1995  | Baquero et al. |
| 5,409,818 | A |   | 4/1995  | Davey et al. |
| 5,468,852 | A |   | 11/1995 | Ohashi et al. |
| 5,475,098 | A |   | 12/1995 | Hall et al. |
| 5,486,454 | A |   | 1/1996  | Madonna et al. |
| 5,495,008 | A |   | 2/1996  | Lane et al. |
| 5,516,898 | A |   | 5/1996  | Ohashi et al. |
| 5,523,205 | A |   | 6/1996  | Cossart et al. |
| 5,525,718 | A |   | 6/1996  | Ohashi et al. |
| 5,529,910 | A |   | 6/1996  | Ohashi et al. |
| 5,541,308 | A | * | 7/1996  | Hogan et al. ............... 536/23.1 |
| 5,574,145 | A |   | 11/1996 | Barry et al. |
| 5,587,286 | A |   | 12/1996 | Pahuski et al. |
| 5,610,012 | A |   | 3/1997  | Luchansky et al. |
| 5,618,666 | A |   | 4/1997  | Popoff et al. |
| 5,652,102 | A |   | 7/1997  | Fratamico et al. |
| 5,654,144 | A |   | 8/1997  | Mann et al. |
| 5,654,417 | A |   | 8/1997  | Tarr et al. |
| 5,656,740 | A |   | 8/1997  | Grosz et al. |
| 5,660,981 | A |   | 8/1997  | Grosz et al. |
| 5,681,716 | A |   | 10/1997 | Popoff et al. |
| 5,683,883 | A |   | 11/1997 | Ohashi et al. |
| 5,705,332 | A |   | 1/1998  | Roll |
| 5,708,160 | A |   | 1/1998  | Goh et al. |
| 5,723,294 | A |   | 3/1998  | Glass et al. |
| 5,733,724 | A |   | 3/1998  | Burbert et al. |
| 5,738,995 | A |   | 4/1998  | Wu et al. |
| 5,747,256 | A |   | 5/1998  | Yan et al. |
| 5,747,257 | A |   | 5/1998  | Jensen |
| 5,753,467 | A |   | 5/1998  | Jensen et al. |
| 5,756,293 | A |   | 5/1998  | Hall et al. |
| 5,756,701 | A |   | 5/1998  | Wu et al. |
| 5,795,717 | A |   | 8/1998  | Nakayama et al. |
| 5,804,378 | A |   | 9/1998  | Popoff et al. |
| 5,824,795 | A |   | 10/1998 | Popoff et al. |
| 5,827,661 | A |   | 10/1998 | Blais |
| 5,843,650 | A |   | 12/1998 | Segev |
| 5,846,783 | A |   | 12/1998 | Wu et al. |
| 5,853,987 | A |   | 12/1998 | Guo et al. |
| 5,922,536 | A |   | 7/1999  | Nivens et al. |
| 5,922,538 | A |   | 7/1999  | Hazel et al. |
| 5,925,522 | A |   | 7/1999  | Wong et al. |
| 5,932,415 | A |   | 8/1999  | Schubert et al. |
| 5,958,686 | A |   | 9/1999  | Houng |
| 5,989,821 | A |   | 11/1999 | Goh et al. |
| 5,989,841 | A |   | 11/1999 | Popoff et al. |
| 5,994,066 | A |   | 11/1999 | Bergeron et al. |
| 6,001,564 | A |   | 12/1999 | Bergeron et al. |

(Continued)

FOREIGN PATENT DOCUMENTS

EP 0605003 A2 12/1993

(Continued)

OTHER PUBLICATIONS

Ahern(The Scientist vol. 9 #15, p. 20, Jul. 24, 1995).*

(Continued)

*Primary Examiner*—Carla J. Myers
*Assistant Examiner*—Katherine Salmon
(74) *Attorney, Agent, or Firm*—Hamilton, DeSanctis & Cha

(57) ABSTRACT

A method for detecting a *Salmonella* species, *E. coli* O157:H7, or *Listeria monocytogenes* is disclosed. The method involves amplifying a genomic nucleotide sequence of a corresponding species and detecting the amplification product. Various primers and probes that can be used in the method are also disclosed. In one embodiment, the amplification step of the method is accomplished by real-time PCR and the amplification product is detected by fluorescence resonance energy transfer using a pair of labeled polynucleotides.

6 Claims, No Drawings

U.S. PATENT DOCUMENTS

| | | | |
|---|---|---|---|
| 6,004,747 | A | 12/1999 | Olsen |
| 6,027,889 | A | 2/2000 | Barany et al. |
| 6,028,187 | A | 2/2000 | Hogan |
| 6,060,252 | A | 5/2000 | Hellyer et al. |
| 6,150,517 | A | 11/2000 | Hogan et al. |
| 6,165,721 | A | 12/2000 | Rostkowski et al. |
| 6,165,724 | A | 12/2000 | Fukushima et al. |
| 6,174,670 | B1 * | 1/2001 | Wittwer et al. ............... 435/6 |
| 6,207,385 | B1 | 3/2001 | Stanley |
| 6,207,818 | B1 | 3/2001 | Hellyer et al. |
| 6,218,110 | B1 | 4/2001 | Nakayama et al. |
| 6,251,607 | B1 | 6/2001 | Tsen et al. |
| 6,268,143 | B1 | 7/2001 | Oberst |
| 6,268,148 | B1 | 7/2001 | Barany et al. |
| 6,284,466 | B1 | 9/2001 | Benson |
| 6,291,168 | B1 | 9/2001 | Musso |
| 6,312,930 | B1 | 11/2001 | Tice, Jr. et al. |
| 6,322,985 | B1 | 11/2001 | Kashi et al. |
| 6,365,723 | B1 * | 4/2002 | Blattner et al. ............ 536/23.1 |
| 6,372,424 | B1 | 4/2002 | Brow et al. |
| 2001/0031470 | A1 | 10/2001 | Shultz et al. |
| 2001/0055759 | A1 | 12/2001 | Kathariou et al. |
| 2002/0055101 | A1 | 5/2002 | Bergeron et al. |
| 2002/0086289 | A1 | 7/2002 | Straus |
| 2002/0090626 | A1 | 7/2002 | Hyldig-Nielson |

FOREIGN PATENT DOCUMENTS

| | | |
|---|---|---|
| EP | 1 138 786 A2 | 9/1995 |
| EP | 0 675 969 B1 | 12/1997 |
| EP | 0 804 616 B1 | 6/2002 |
| JP | 03049698 A | 3/1991 |
| JP | 200000931981 A | 4/2000 |
| US | WO9740161 * | 10/1997 |
| WO | WO 89/06699 | 7/1969 |
| WO | WO 90/08841 | 8/1990 |
| WO | WO 90/14444 | 11/1990 |
| WO | WO 94/13832 | 6/1994 |
| WO | WO 97/32043 | 9/1997 |
| WO | WO 98/20148 | 5/1998 |
| WO | WO 98/20160 | 5/1998 |
| WO | WO 98/36096 | 8/1998 |
| WO | WO 99/51771 | 10/1999 |
| WO | WO 00/14276 | 3/2000 |
| WO | WO 00/77247 | 12/2000 |
| WO | WO 01/12853 A1 | 2/2001 |

OTHER PUBLICATIONS

Homo sapiens genomic sequence surrounding NotI site, clone NB6-490S, accession #AJ325628 (bp518-154).*

McGraw et al. *E. coli.* enterohermorrhagic strain DEC 3f gamma intimin ea gene complete cds(Accession number AF081182, Jan. 1999).* van den Bergh et al.(Clinical Chemistry 46, No. 8, 2000).*

Homo sapiens genomic sequence surrounding NotI site, clone NB1-172S, accession #AJ330656(bp130-148).*

McGraw et al. Mol. Biol. Evol. 1999 vol. 16 p. 12-22.*

Sharma, V. K., "Development and Application of a Real-Time PCR to Detect and Quantify Enterohemorrhagic *Escherichia coli* O157:H7 and Other Shiga Toxin-Producing *E. coli*," Abstracts of the General Meeting of the American Society for Microbiology, vol. 101, p. 573, XP-008038498, May 23, 2001, *abstract*.

Koo, K. et al., "Detection of *Listeria monocytogenes* by Fluorescence Resonance Energy Transfer-Based PCR with an Inexpensive 'Asymmetric ' Fluorogenic Probe Set," Abstracts of the General Meeting of the American society for Microbiology, vol. 100, p. 515, XP-008038497, May 22, 2000, *abstract*.

Chen, W., et al., "Molecular Beacons: A Real-Time Polymerase Chain Reaction Assay for Detecting *Samonella*," Analytical Biochemistry, vol. 280, pp. 166-172, XP-002315701, 2000, *whole document*.

Nogva, H. K., et al., "Application of 5'-Nuclease PCR for Quantitative Detection of *Listeria monocytogenes* in Pure Cultures, Water, Skim Milk, and Unpasteurized Whole Milk," Applied and Enviromental Microbiology, Washington, D.C., vol. 66, No. 10, pp. 4266-4271, XP-002242217, ISSN: 0099-2240/00, Oct. 2000, *whole document*.

Fortin, N. Y. et al., "Use of Real-Time Polymerase Chain Reaction and Molecular Beacons for the Detection of *Escherichia coli* O157:H7," Analytical Biochemistry, Academic Press, New York, NY, vol. 289, No. 2, pp. 281-288, XP-002250269, ISSN: 0003-2697/01, Feb. 15, 2001, *whole document*.

Kaniga et al., Database GenEmbl Accession No. U25631, "*Salmonella typhimurium* invasin homologs SicA (sicA), SipB (sipB), and SipC (sipC) genes, complete cds," Sep. 1995.

McGraw et al., Database GenEmbl Accession No. AF081182, "*Escherichia coli* enterohemorrhagic strain DEC 3a gamma intimin (eae) gene, complete cds," Jan. 1999.

Hain et al., Database GenEmbl Accession No. AJ012346, "*Listeria moncytogenes* internalin operon; orfA, inlA, and inlB genes," Jan. 2001.

Sharma et al., "Simultaneous detection of *Salmonella* strains and *Escherichia coli* 0157:H7 with fluorogenic PCR and single-enrichment-broth culture." Applied and Enviromental Microbiology, vol. 66, No. 12, pp. 5472-5476, Dec. 2000. (See entire reference, especially p. 5472).

Carlson et al., "Detection of multiresistant *Salmonella typhimurium* DT104 using multiplex and fluorogenic PCR." Molecular and Cellular Probes, vol. 13, No. 3, pp. 213-222, Jun. 1999. (See entire reference, especially Table 1).

Elenitoba-Johnson et al., "Multiplex PCR by multicolor fluorimetry and fluoroscence melting curve analysis," Nature Medicine, vol. 7, No. 2, pp. 249-253, Feb. 2001 (Especially pp. 5/12 and 7/12).

Ahern, "Biochemical, reagent kits offer scientists good return on investment," The Scientist, vol. 9, No. 15, pp. 1-5, Jul. 1995. (Especially pp. 4/5).

Bellin et al., "Rapid Detection of Enterohemorrhagic *Escherichia coli* by Real-Time PCR with fluorescent hybridization probes," Journal of Clinical Microbiology, vol. 39, No. 1, pp. 370-374, Jan. 2001. (Especially p. 370).

* cited by examiner

METHODS AND OLIGONUCLEOTIDES FOR THE DETECTION OF *SALMONELLA* SP., *E. COLI* O157:H7, AND *LISTERIA MONOCYTOGENES*

CROSS-REFERENCE TO RELATED APPLICATION

This application claims the benefit of U.S. application Ser. No. 60/300,199, filed on Jun. 22, 2001, U.S. application Ser. No. 60/373,588, filed on Apr. 18, 2002, and U.S. application Ser. No. 60/373,589, filed on Apr. 18, 2002.

STATEMENT REGARDING FEDERALLY SPONSORED RESEARCH OR DEVELOPMENT

None.

BACKGROUND OF THE INVENTION

Federal and state health and safety standards mandate that industrial food service companies and manufacturing facilities perform routine testing for common bacteria, such as *Salmonella* species, *E. coli* O157:H7, and *Listeria monocytogenes*, that cause food-borne illnesses. As a safety precaution, companies are required to perform testing on each batch or lot of food prior to the food reaching the public. Several methods are currently available for industrial testing of bacteria in the food service industry.

However, there are currently severe limitations on the tests available to the industry. Present methods utilized as industry standards require 2-5 days to perform. For example, the most widely used methods for detection of *Salmonella* employ a pre-enrichment (day 1), a selective enrichment (day 2), and a final enrichment followed by an immunoassay requiring $10^5$ organisms (day 3); the most widely used methods of detection of *E. coli* O157:H7 employ a selective enrichment (8-28 hours) and an immunoassay requiring $10^5$ organisms; the most widely used methods of detection of *Listeria monocytogenes* employ a pre-enrichment (26-30 hours), an enrichment (22-26 hours), and an immunoassay requiring $10^5$ organisms. For the detection of *E. coli* O157: H7 and *Listeria monocytogenes*, all samples that are suspected as positive by the immunoassay must be confirmed by culture methods (1-3 days for *E. coli* O157:H7 and 4-5 days for *Listeria monocytogenes*). Thus, in many cases, the food suppliers must wait days for test results before shipping their already manufactured products. As a result, the company may lose profits from a reduced shelf life and the wait also increases the potential for food spoilage.

In addition, using methods now available in the art, the organism needs to be cultured to a concentration of at least $10^5$/ml to be detected. Because the margin of error in detectability of the bacteria is high, false negative tests may result and a food poisoning outbreak may occur. The company is then forced to recall product that has already reached the consumer. This places the public at a great health risk. The manufacturer or producer is also forced to bear the costs of recall, and is at a risk for lawsuit or government mandated shutdown of production facilities.

Thus, there is a need for an inexpensive testing technology that provides a rapid turn-around time, and a high degree of accuracy and reproducibility, which will result in safer food manufacturing and preparation. Additionally, there is a need for a method that keeps pace with new manufacturing processes. Polymerase chain reaction ("PCR") testing technology for food-borne pathogenic bacteria facilitates rapid and accurate testing for the manufacturers.

BRIEF SUMMARY OF THE INVENTION

The present invention provides a method for detecting a *Salmonella* species, *E. coli* O157:H7, or *Listeria monocytogenes*. The method involves amplifying a genomic nucleotide sequence of a corresponding species and detecting the amplification product. The present invention also encompasses primers and probes that can be used in the method. The primers and probes can be provided in a detection kit.

In one embodiment, the amplification step of the method of the present invention is accomplished by real-time PCR and the amplification product is detected by fluorescence resonance energy transfer using a pair of labeled oligonucleotides.

It is a feature of the present invention that the genomic region from which a nucleotide sequence is amplified is involved in bacterial virulence.

It is an advantage of the present invention that the method of bacteria detection is sensitive.

It is another advantage of the present invention that the method of bacteria detection is fast.

Other objects, advantages, and features of the present invention will become apparent from the following detailed description of the invention.

BRIEF DESCRIPTION OF THE SEVERAL VIEWS OF THE DRAWINGS

Not applicable.

DETAILED DESCRIPTION OF THE INVENTION

The present invention relates to the detection of bacterial pathogens in food or other materials with much greater sensitivity and speed than was heretofore possible. Primers have been identified which permit a rapid and sensitive type of polymerase chain reaction (PCR) to amplify target DNA if, and only if, one of the target pathogens is present in a sample. Probes are also identified which will bind to the amplified DNA products produced again if, and only if, the organism is present. The method has been implemented for *Salmonella*, *E. coli* O157:H7, and *Listeria monocytogenes*.

An used herein, an "isolated nucleic acid" is a nucleic acid which may or may not be identical to that of a naturally occurring nucleic acid but which is isolated from a living host organism. When "isolated nucleic acid" is used to describe a primer or a probe, the nucleic acid is not identical to the structure of a naturally occurring nucleic acid spanning at least the length of a gene.

In one aspect, the present invention relates to nucleic acids that can be used as primers to amplify a genomic fragment isolated from *Salmonella* species, *E. coli* O157:H7 or *Listeria monocytogenes* to detect the corresponding species. Such a nucleic acid has a nucleotide sequence containing at least 12 consecutive nucleotides of SEQ ID NO:1 (5' primer for *Salmonella* species), SEQ ID NO:2 (3' primer for *Salmonella* species), SEQ ID NO:5 (5' primer for *E. coli* O157:H7), SEQ ID NO:6 (3' primer for *E. coli* O157:H7), SEQ ID NO:9 (5' primer for *Listeria monocytogenes*), or SEQ ID NO:10 (3' primer for *Listeria monocytogenes*).

Preferably, the nucleic acid has a sequence that contains at least 15 or 18 consecutive nucleotides, and most preferably the fill length, of the above-identified sequences.

In another aspect, the present invention relates to labeled nucleic acids that can act as probes to facilitate the detection of an amplification product of a *Salmonella* species, *E. coli* O157:H7 or *Listeria monocytogenes*, obtained using the primers described above. The labeled nucleic acid probes work in pairs. One probe in each pair is labeled at the 3' end and the other probe is labeled at the 5' end. Each probe pair hybridize to the same strand of the amplification product. When hybridized to the amplification product, the 3' end nucleotide of the 3' end labeled nucleic acid probe and the 5' end nucleotide of the 5' end labeled nucleic acid probe are less than six nucleotides apart so that energy transfer occurs between the two labels resulting in an emission intensity change of at least one of the labels. The emission intensity change indicates the presence of the amplification product.

The labeled nucleic acid probes in each pair have nucleotide sequences containing at least 12 consecutive nucleotides of SEQ ID NO:13 (for *Salmonella* species), the complement of SEQ ID NO:13 (for *Salmonella* species), SEQ ID NO:14 (for *E. coli* O157:H7), the complement of SEQ ID NO:14 (for *E. coli* O157:H7), SEQ ID NO:15 (for *Listeria monocytogenes*), or the complement of SEQ ID NO:15 (for *Listeria monocytogenes*). Preferably, the labeled nucleic acids in each probe pair have nucleotide sequences containing at least 15 or 18 nucleotides of the above-identified sequences. Most preferably, the labeled nucleic acids in each pair have the following pair of nucleotide sequences: SEQ ID NO:3 and SEQ ID NO:4 (for *Salmonella* species), the complement of SEQ ID NO:3 and the complement of SEQ ID NO:4 (for *Salmonella* species), SEQ ID NO:7 and SEQ ID NO:8 (for *E. coli* O157:H7), the complement of SEQ ID NO:7 and the complement of SEQ ID NO:8 (for *E. coli* O157:H7), SEQ ID NO:11 and SEQ ID NO:12 (for *Listeria monocytogenes*), and the complement of SEQ ID NO:11 and the complement of SEQ ID NO:12 (for *Listeria monocytogenes*).

Any pair of labeling molecules that can undergo energy transfer when located close to each other (less than 6 nucleotides apart on a nucleotide sequence) to cause a change in emission intensity in at least one of the labeling molecules can be used to make the labeled nucleic acids described above. An example of a labeling molecule for one nucleic acid in a pair includes, but are not limited to, fluorescein. Examples of labeling molecules for the other nucleic acid in the pair include but are not limited to LC RED 640 (Roche Lightcycler), LC RED 705 (Roche Lightcycler).

In another aspect, the present invention relates to a kit for detecting at least one of a *Salmonella* species, *E. coli* O157:H7 and *Listeria monocytogenes*. The kit contains a pair of nucleic acid primers and a pair of labeled nucleic acids, as described above, for one, two or all three of the above species. Other reagents for the amplification of a target DNA and the detection of the amplification product can also be included in the kit. The kit may also include positive and negative controls for the above species. The positive control can be any sample that contains a target DNA to be amplified, including the bacteria themselves, at an amount over the detection limit. The negative control is a sample that does not contain the target DNA to be amplified.

In another aspect, the present invention relates to an isolated nucleic acid the amplification of which allows detection of a *Salmonella* species, *E. coli* O157:H7 or *Listeria monocytogenes*. Examples of such nucleic acids include those that contain SEQ ID NO:13, SEQ ID NO:14 or SEQ ID NO:15.

In still another aspect, the present invention relates to a method for detecting a *Salmonella* species, *E. coli* O157:H7, or *Listeria monocytogenes*. The method involves amplifying a fragment of the genomic DNA specific to the above species and detecting the amplification product. Unique sequences that can be used to identify a *Salmonella* species, *E. coli* O157:H7, and *Listeria monocytogenes* include nucleotide 2314 to nucleotide 2047 (nucleotide 9 to nucleotide 243 of SEQ ID NO:13) of the sipB-sipC region of the *Salmonella* genome (GenBank Accession No. U25631), nucleotide 1185 to nucleotide 1532 (nucleotide 7 to nucleotide 354 of SEQ ID NO:14) of the eae gene of *E. coli* O157:H7 (GenBank Accession No. AF081182), and nucleotide 2995 to nucleotide 3196 (nucleotide 9 to nucleotide 210 of SEQ ID NO:15) of the internalin operon of *Listeria monocytogenes* (GenBank Accession No. AJ012346). Any genomic fragments that contain the above sequences can be amplified for detecting the above species. Given what is disclosed herein, a skilled artisan knows how to amplify a fragment that contains one of the above specific sequences and then detect the presence of an amplification product that contains the sequence. Examples of the primers that can be used in the method of present invention are described above.

The genomic sequences amplified and detected with the method of the present invention are from genomic regions that are involved in bacterial virulence. The sip proteins of the *Salmonella* species and the internalin proteins of *Listeria monocytogenes* are required for cell invasion; the EAE proteins of *E. coli* O157:H7 are required for cell effacement and attachment. Thus, the method of the present invention detects bacteria that harbor virulent traits. Nonpathogenic strains of these species are not meant to be detected using this technique.

It is understood that the species specific sequences actually amplified in performing the method of the present invention may vary somewhat from the sequences described above. The variations may be caused by sequencing errors, strain-specific variations or some other reasons. The method of the present invention intends to encompass these variations.

In a specific embodiment, a fragment of genomic DNA specific to a species is amplified by real-time PCR and the amplification product is detected by fluorescence resonance energy transfer (FRET) using labeled nucleic acids described above as internal hybirdization probes. In this embodiment, internal hybridization probes are included in the PCR reaction mixture so that product detection occurs as the product is formed, further reducing post-PCR processing time. Roche Lightcycler PCR instrument (U.S. Pat. No. 6,174,670) or other real-time PCR instruments can be used in this embodiment of the invention. PCR amplification of DNA allows for the increase in sensitivity to less than $10^1$ organisms in comparison to $10^5$ organisms in standard immuno-detection methods presently used. Real-time PCR amplification and detection can reduce total assay time so that test results can be obtained within 12 hours.

The invention will be more fully understood upon consideration of the following non-limiting examples.

EXAMPLE 1

Detection of *Salmonella* species

A sample of the food product was weighed out and mixed with Buffered Peptone Water. The ratio of the food product to Buffered Peptone Water was 25 to 225 (grams to mls). The mixture was then mechanically homogenized and incubated at 35+/−2° C. After six hours of incubation, 15 ml of mixture was removed and centrifuged at 2,500×g for 10 minutes. The supernatant was discarded and the pellet was resuspended in 200 ml of TE. The DNA was then extracted from the bacteria using either the Qiagen QIAamp DNA mini kit (Qiagen Inc., Valencia, Calif.) or Biotecon foodproof® extraction kit (Potsdam, Germany).

Next, PCR amplification and detection of amplification product were performed. The following oligonucleotides were designed to provide for the PCR amplification of a 250 bp product spanning from base 2305 to base 2555 of the sipB-sipC region of the *Salmonella* genome (GenBank Accession #U25631): forward 5'-ACAGCAAAATGCGGATGCTT-3' (SEQ ID NO:1) and reverse 5'-GCGCGCTCAGTGTAGGACTC-3' (SEQ ID NO:2).

In addition, internal hybridization probes were designed to allow for detection of the PCR product by fluorescence resonance energy transfer within the Roche Lightcycler. The sequence and modifications of the probes were: upstream 5'-GCAATCCGTTAGCGCTAAAGATATTCTGAATAGT-Fluorescein-3' (SEQ ID NO:3) and downstream 5'-LC RED640TTGGTATTAGCAGCAGTAAAGTCAGTGACCTGG-Phos-3' (SEQ ID NO:4). These probes were designed to anneal to the upper strand from positions 2464-2497 (upstream) and 2499-2531 (downstream). PCR optimization was then carried out to allow for rapid real-time amplification and detection in the Roche Lightcycler PCR instrument (U.S. Pat. No. 6,174,670). PCR amplification of DNA led to an increase in sensitivity to less than $10^1$ organisms in comparison to $10^5$ organisms in standard prior art immuno detection methods. These hybridization probes provided a high degree of specificity and accurate detection of *Salmonella* isolates. No false positives were observed.

This test methodology detected *Salmonella* at the low pre-enrichment concentration range of $10^0$ organisms/ml-$10^1$ organisms/ml by amplification of DNA using oligonucleotides. Utilizing the Roche Lightcycler, which completed cycles in about 30 minutes, instead of hours or overnight, as in older thermocyclers, allowed test results to be obtained within 12 hours.

EXAMPLE 2

Detection of *E. coli* O157:H7

A sample of the food product was weighed out and mixed with modified Trypticase Soy Broth. The ratio of the food product to modified Trypticase Soy Broth was 25 to 225 (grams to mls). The mixture was then mechanically homogenized and incubated at 35+/−2° C. After six hours of incubation, 15 ml of mixture was removed and centrifuged at 2,500×g for 10 minutes. The supernatant was discarded and the pellet was re-suspended in 200 ml of TE. The DNA was then extracted from the re-suspended bacteria using either the Qiagen QIAamp DNA mini kit (Qiagen Inc., Valencia, Calif.) or Biotecon foodproof® extraction kit (Potsdam, Germany).

Next PCR amplification and detection of PCR amplification product were performed. The following oligonucleotides were designed to provide for the PCR amplification of a 361 bp product spanning from base 1179 to base 1539 of the eae gene of the *E. coli* O157:H7 genome (GenBank Accession #AF081182): forward 5'-TGGTACGGGTAATGAAAA-3' (SEQ ID NO:5) and reverse 5'-AATAGCCTGGTAGTCTTGT-3' (SEQ ID NO:6).

In addition, internal hybridization probes were designed for detection of the PCR product by fluorescence resonance energy transfer within the Roche Lightcycler. The sequence and modifications of the probes were: upstream 5'-CGCAGTCAGGGCGGTCAGA-Fluorescein-3' (SEQ ID NO:7) and downstream 5'-LC RED640TCAGCATAGCGGAAGCCAAA-Phos-3' (SEQ ID NO:8). These probes were designed to anneal to the upper strand from positions 1477-1495 (upstream) and 1497-1516 (downstream). PCR optimization was then carried out to allow for rapid real-time amplification and detection in the Roche Lightcycler PCR instrument (U.S. Pat. No. 6,174,670) or other real-time PCR instrument. PCR amplification of DNA led to an increase in sensitivity to less than $10^1$ organisms in comparison to $10^5$ organisms in standard prior art immuno detection methods. These hybridization probes provided a high degree of specificity and accurate detection of *E. coli* O157:H7 isolates. No false positives were observed.

Utilizing the Roche Lightcycler, which completed cycles in about 30 minutes, instead of hours or overnight, as in older thermocyclers, allowed test results to be obtained within 12 hours.

EXAMPLE 3

Detection of *Listeria monocytogenes*

Two hundred and twenty five ml of Fraser broth was added to a sample of 25 grams of the food product. The mixture was then stomached and incubated at 30° C. After eight hours of incubation, 15 ml of mixture was removed and centrifuged at 2,500×g for 10 minutes. The supernatant was discarded and the pellet was resuspended in 200 ml TE. The DNA was then extracted from the resuspended bacteria using either the Qiagen QIAamp DNA mini kit (Qiagen Inc., Valencia, Calif.) or Biotecon foodproof® extraction kit (Potsdam, Germany).

Next, PCR amplification and detection of PCR amplification product were performed. The following oligonucleotides were designed to provide for the PCR amplification of a 217 bp product spanning from base 2987 to base 3203 of the internalin operon of the *Listeria monocytogenes* genome: forward 5'-ATTTAGTGGAACCGTGACGC-3' (SEQ ID NO:9) and reverse 5'-GATGTCATTTGTCGGCATT-3' (SEQ ID NO:10).

In addition, internal hybridization probes were designed to allow for detection of the PCR product by fluorescence resonance energy transfer within the Roche Lightcycler. The sequence and modifications of the probes were upstream 5'-AGCTAAGCCCGTAAAAGAAGGT-Fluorescein-3' (SEQ ID NO:11) and downstream 5'-LC RED640-ACACATTTGTTGGTTGGTTTGATGCC-Phos-3' (SEQ ID NO:12). These probes were designed to anneal to the upper strand from positions 3098-3119 (upstream) and 3121-3146 (downstream). PCR optimization was then carried out to allow for rapid real-time amplification and detection in the Roche Lightcycler PCR instrument (U.S. Pat. No. 6,174, 670) or other real-time PCR instrument. These hybridization probes provided a high degree of specificity and accurate detection of *Listeria monocytogenes* isolates. No false positives were observed.

Utilizing the Roche Lightcycler, which completed cycles in about 30 minutes, instead of hours or overnight, as in older thermocyclers, allowed test results to be obtained within 12 hours.

The present invention is not intended to be limited to the foregoing examples, but encompasses all such modifications and variations as come within the scope of the appended claims.

We claim:

1. An isolated nucleic acid selected from the group consisting of SEQ ID NO: 5, SEQ ID NO: 6, SEQ ID NO: 7, SEQ ID NO: 8, and the complements thereof.

2. A kit for detecting the presence of *E. coli* O157:H7, said kit comprising a primer pair and a pair of labeled probes, wherein the primer pair consists of SEQ ID: 5 and SEQ ID NO: 6 or the complements thereof, and the pair of labeled probes consists of a first probe consisting of SEQ ID NO: 7, or the complement thereof, and a label at the 3' end and a second probe consisting of SEQ ID NO: 8, or the complement thereof, and a label at the 5' end.

3. The kit of claim 2, wherein the first probe is labeled with fluorescein and the second probe is labeled with LC RED 640 or LC RED 705.

4. A method for detecting the presence of *E. coli* O157: H7, said method comprising:
   (a) obtaining a sample and amplifying at least a portion of the eae gene of *E. coli* O157: H7 with a primer pair consisting of SEQ ID NO: 5 and SEQ ID NO: 6 or the complements thereof in the presence of a pair of labeled probes such that said amplification step produces an amplified eae gene product if the sample comprises at least a portion of the eae gene of *E. Coli* O 157: H7 that comprises the nucleotide sequence of the primer pair, wherein the pair of labeled probes consists of a first probe consisting of SEQ ID NO: 7, or the complement thereof, and a donor fluorophore of a fluorescence resonance energy transfer pair at the 3' end and a second probe consisting of SEQ ID NO: 8, or the complement thereof, and an acceptor fluorophore of a fluorescence resonance energy transfer pair at the 5' end, such that upon hybridization of the first and second probes with the amplified eae gene product, the donor and the acceptor fluorophores are less than 6 nucleotides apart from one another; and
   (b) detecting the presence or absence of fluorescence resonance energy transfer (FRET) between the donor fluorophore and the acceptor fluorophore,
   wherein the presence of FRET is indicative of the presence of *E. coli* O157: H7 in the sample.

5. The method of claim 4, wherein the donor fluorophore is fluoroscein.

6. The method of claim 4, wherein the acceptor fluorophore is LC RED 640 or LC RED 705.

* * * * *

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:PCR primer
      for Salmonella sp.

<400> SEQUENCE: 1
acagcaaaat gcggatgctt                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:PCR primer
      for Salmonella sp.

<400> SEQUENCE: 2
gcgcgctcag tgtaggactc                                                     20

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:Detection
      probe for Salmonella sp.

<400> SEQUENCE: 3
gcaatccgtt agcgctaaag atattctgaa tagt                                     34

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:Detection
      probe for Salmonella sp.

<400> SEQUENCE: 4
ttggtattag cagcagtaaa gtcagtgacc tgg                                      33

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:PCR primer
      for E. coli O157:H7

<400> SEQUENCE: 5
tggtacgggt aatgaaaa                                                       18
```

```
<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:PCR primer
      for E. coli O157:H7

<400> SEQUENCE: 6
aatagcctgg tagtcttgt                                                   19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:Detection
      probe for E. coli O157:H7

<400> SEQUENCE: 7
cgcagtcagg gcggtcaga                                                   19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Detection
      probe for E. coli O157:H7

<400> SEQUENCE: 8
tcagcatagc ggaagccaaa                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:PCR primer
      for Listeria monocytogenes

<400> SEQUENCE: 9
atttagtgga accgtgacgc                                                  20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:PCR primer
      for Listeria monocytogenes

<400> SEQUENCE: 10
gatgtcattt gtcggcatt                                                   19

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:Detection
      probe for Listeria monocytogenes

<400> SEQUENCE: 11
agctaagccc gtaaaagaag gt                                               22
```

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:Detection
      probe for Listeria monocytogenes

<400> SEQUENCE: 12
acacatttgt tggttggttt gatgcc                                       26

<210> SEQ ID NO 13
<211> LENGTH: 251
<212> TYPE: DNA
<213> ORGANISM: Salmonella sp.
<220> FEATURE:
<221> NAME/KEY: misc_feature
<222> LOCATION: (1)..(251)
<223> OTHER INFORMATION: Fragment of sipB-sipC region

<400> SEQUENCE: 13
acagcaaaat gcggatgctt cgcgttttat tctgcgccag agtcgcgcat aaaaactgcc    60
aaaataaagg gagaaaaata tgttaattag taatgtggga ataaatcccg ccgcttattt   120
aaataatcat tctgttgaga atagttcaca gacagcttcg caatccgtta gcgctaaaga   180
tattctgaat agtattggta ttagcagcag taaagtcagt gacctggggt tgagtcctac   240
actgagcgcg c                                                       251

<210> SEQ ID NO 14
<211> LENGTH: 361
<212> TYPE: DNA
<213> ORGANISM: E. coli O157:H7
<220> FEATURE:
<221> NAME/KEY: misc_feature
<222> LOCATION: (1)..(361)
<223> OTHER INFORMATION: Fragment of eae gene

<400> SEQUENCE: 14
tggtacgggt aatgaaaatg atctcccttta ctcaatgcag ttccgttatc agtttgataa    60
atcgtggtct cagcaaattg aaccacagta tgttaacgag ttaagaacat tatcaggcag   120
ccgttacgat ctggttcagc gtaataacaa tattattctg gagtacaaga agcaggatat   180
tctttctctg aatattccgc atgatattaa tggtactgaa cacagtacgc agaagattca   240
gttgatcgtt aagagcaaat acggtctgga tcgtatcgtc tgggatgata gtgcattacg   300
cagtcagggc ggtcagattc agcatagcgg aagccaaagc gcacaagact accaggctat   360
t                                                                  361

<210> SEQ ID NO 15
<211> LENGTH: 217
<212> TYPE: DNA
<213> ORGANISM: Listeria monocytogenes
<220> FEATURE:
<221> NAME/KEY: misc_feature
<222> LOCATION: (1)..(217)
<223> OTHER INFORMATION: Fragment of internalin operon

<400> SEQUENCE: 15
atttagtgga accgtgacgc agccacttaa ggcaattttt aatgttaagt ttcatgtgga    60
cggcaaagaa acaaccaaag aagtggaagc tgggaattta ttgactgaac cagctaagcc   120

-continued

```
cgtaaaagaa ggtcacacat ttgttggttg gtttgatgcc caaacaggcg gaactaaatg      180
gaatttcagt acggataaaa tgccgacaaa tgacatc                                217
```